(12) United States Patent
Glenn (10) Patent No.: US 8,282,610 B1
(45) Date of Patent: Oct. 9, 2012

(54) STABILIZED IMPLANTABLE VASCULAR ACCESS PORT

(75) Inventor: Bradley J. Glenn, Oneida, WI (US)

(73) Assignee: Stealth Therapeutics, Inc., Madison, WI (US)

( * ) Notice: Subject to any disclaimer, the term of this patent is extended or adjusted under 35 U.S.C. 154(b) by 0 days.

(21) Appl. No.: 12/661,576

(22) Filed: Mar. 18, 2010

Related U.S. Application Data (62) Division of application No. 11/651,770, filed on Jan. 9, 2007, now Pat. No. 7,708,722.

(60) Provisional application No. 60/757,417, filed on Jan. 10, 2006.

(51) Int. Cl.
*A61M 37/00* (2006.01)

(52) U.S. Cl. .............. 604/288.02; 604/288.01; 604/104; 604/175

(58) Field of Classification Search .......... 604/104–109, 604/164.01–165.01, 288.01–288.04, 174–178
See application file for complete search history.

(56) References Cited

U.S. PATENT DOCUMENTS

| | | |
|---|---|---|
| 837,085 A | 11/1906 | Loar |
| 1,434,964 A | 11/1922 | Rose |
| 1,733,189 A | 10/1929 | Friedman |
| 3,397,699 A | 8/1968 | Kohl |
| 3,692,029 A | 9/1972 | Adair |
| 3,713,447 A | 1/1973 | Adair |
| 3,938,530 A | 2/1976 | Santomieri |
| 3,951,147 A | 4/1976 | Tucker |
| 4,043,338 A | 8/1977 | Homm |
| 4,077,412 A | 3/1978 | Moossun |
| 4,543,088 A | 9/1985 | Bootman |
| 4,569,675 A | 2/1986 | Prosl |
| 4,604,090 A | 8/1986 | Renicke |
| 4,608,965 A | 9/1986 | Anspach, Jr. |
| 4,626,244 A | 12/1986 | Renicke |
| 4,627,838 A | 12/1986 | Cross |
| 4,673,394 A | 6/1987 | Fenton, Jr. |
| 4,704,103 A | 11/1987 | Stober |
| 4,743,231 A | 5/1988 | Kay |
| 4,772,270 A | 9/1988 | Wiita |
| 4,778,452 A | 10/1988 | Moden |

(Continued)

OTHER PUBLICATIONS

Hyoung Il Na et al. Fixation Methods for Implantable Port Chamber: Comparative Study Using Glue, Self-Stabilizing Leg and Suture Fixations in Rabbits. Korean J Radio 2004; 5; 266-273.*

(Continued)

*Primary Examiner* — Theodore Stigell
*Assistant Examiner* — Leah Stohr
(74) *Attorney, Agent, or Firm* — Heisler & Associates (57) ABSTRACT

The subcutaneously implantable vascular access port has two parts including a body and a wing. The body supports a chamber covered by a septum, with a septum held in place over the chamber by a collar. The chamber is coupleable to a vascular structure, such as through tubing extending from the body, for delivery of medical preparations. The body is preferably elongate in form. The wing is configured to be adjustable in width. In one embodiment the wing rotates relative to the body and has an elongate form similar to that of the body. When the wing is rotated it extends laterally from the body and enhances a stability of the body. In another embodiment, the wing is provided as a deformable wing which can expand laterally out of side openings of a cavern in the body into which the deformable wing is inserted.

4 Claims, 6 Drawing Sheets

U.S. PATENT DOCUMENTS

| | | |
|---|---|---|
| 4,802,885 A | 2/1989 | Weeks |
| 4,880,414 A | 11/1989 | Whipple |
| 4,995,868 A | 2/1991 | Brazier |
| 5,090,954 A | 2/1992 | Geary |
| 5,092,849 A | 3/1992 | Sampson |
| 5,108,377 A | 4/1992 | Cone |
| 5,112,310 A | 5/1992 | Grobe |
| 5,113,846 A | 5/1992 | Hiltebrandt |
| 5,167,638 A | 12/1992 | Felix |
| 5,215,103 A | 6/1993 | Desai |
| 5,217,450 A | 6/1993 | Pryor |
| 5,217,451 A | 6/1993 | Freitas |
| 5,275,610 A | 1/1994 | Eberbach |
| 5,279,565 A | 1/1994 | Klein |
| 5,306,226 A | 4/1994 | Salama |
| 5,332,398 A | 7/1994 | Miller |
| 5,338,297 A | 8/1994 | Kocur |
| 5,344,439 A | 9/1994 | Otten |
| 5,356,382 A | 10/1994 | Picha |
| 5,360,407 A | 11/1994 | Leonard |
| 5,365,926 A | 11/1994 | Desai |
| 5,387,192 A | 2/1995 | Glantz |
| 5,399,168 A | 3/1995 | Wadsworth, Jr. |
| 5,421,832 A | 6/1995 | Lefebvre |
| 5,443,449 A | 8/1995 | Buelna |
| 5,454,365 A | 10/1995 | Bonutti |
| 5,527,336 A | 6/1996 | Rosenbluth |
| 5,547,458 A | 8/1996 | Ortiz |
| 5,562,618 A | 10/1996 | Cai |
| 5,624,395 A | 4/1997 | Mikhail |
| 5,624,399 A | 4/1997 | Ackerman |
| 5,632,729 A | 5/1997 | Cai |
| 5,688,247 A * | 11/1997 | Haindl et al. ............. 604/175 |
| 5,695,479 A | 12/1997 | Jagpal |
| 5,716,326 A | 2/1998 | Dannan |
| 5,833,654 A | 11/1998 | Powers |
| 5,848,989 A | 12/1998 | Villani |
| 5,906,596 A | 5/1999 | Tallarida |
| 5,957,900 A | 9/1999 | Ouchi |
| 5,971,954 A | 10/1999 | Conway |
| 5,989,216 A | 11/1999 | Johnson |
| 5,990,382 A | 11/1999 | Fox |
| 6,030,406 A | 2/2000 | Davis |
| 6,080,142 A | 6/2000 | Sachse |
| 6,099,506 A | 8/2000 | Macoviak |
| 6,190,352 B1 | 2/2001 | Haarala |
| 6,213,973 B1 | 4/2001 | Eliasen |
| 6,355,020 B1 | 3/2002 | Bousquet |
| 6,409,674 B1 | 6/2002 | Brockway |
| 6,485,473 B1 | 11/2002 | Lynn |
| 6,569,150 B2 | 5/2003 | Teague |
| 6,572,587 B2 | 6/2003 | Lerman |
| 6,601,795 B1 | 8/2003 | Chen |
| 6,623,448 B2 | 9/2003 | Slater |
| 6,629,953 B1 | 10/2003 | Boyd |
| 6,629,956 B1 | 10/2003 | Polidoro |
| 6,699,216 B2 | 3/2004 | Ikeguchi |
| 6,758,831 B2 | 7/2004 | Ryan |
| 6,780,175 B1 | 8/2004 | Sachdeva |
| 6,893,418 B2 | 5/2005 | Liu |
| 6,929,621 B2 | 8/2005 | Whitmore |
| 6,997,885 B2 | 2/2006 | Lubock |
| 6,997,909 B2 | 2/2006 | Goldberg |
| 6,997,914 B2 | 2/2006 | Smith |
| 7,037,321 B2 | 5/2006 | Sachdeva |
| 2001/0049492 A1 | 12/2001 | Frazier |
| 2002/0165553 A1 | 11/2002 | Elbert |
| 2002/0177806 A1 | 11/2002 | Meier |
| 2002/0177814 A1 | 11/2002 | Meng |
| 2003/0014009 A1 | 1/2003 | Kletschka |
| 2004/0078004 A1 | 4/2004 | Bourne |
| 2004/0249342 A1 | 12/2004 | Khosravi |
| 2004/0254537 A1 | 12/2004 | Conlon |
| 2005/0043735 A1 | 2/2005 | Ahmad |
| 2005/0075644 A1 | 4/2005 | DiPoto |
| 2005/0113929 A1 | 5/2005 | Cragg |
| 2005/0119617 A1 | 6/2005 | Stecker |
| 2005/0131383 A1 | 6/2005 | Chen |
| 2005/0177105 A1 | 8/2005 | Shalev |
| 2005/0251168 A1 | 11/2005 | Hess |
| 2006/0217673 A1 * | 9/2006 | Schulze et al. ........... 604/288.02 |
| 2007/0088258 A1 | 4/2007 | Wenchell |
| 2007/0088259 A1 | 4/2007 | Chu |
| 2007/0276493 A1 | 11/2007 | Malandain |

OTHER PUBLICATIONS

James C. Andrews, MD et al.; Long-Term Central Venous Access with a Peripherally Placed Subcutaneous Infusion Port: Initial Results; Radiology; Jul. 1990; pp. 45-47; vol. 176, No. 1.

Ernst-Peter K.Strecker, MD et al.; Percutaneously Implantable Catheter-Port System: Preliminary Technical Results; Radiology; Feb. 1997; pp. 574-577; vol. 202, No. 2.

Hyoung Il Na, MD et al.; Fixation Methods for Implantable Port Chamber: Comparative Study Using Glue, Self-Stabilizing Leg and Suture Fixations in Rabbits; Korean J Radiol 5(4); Dec. 2004; pp. 266-273.

* cited by examiner

STABILIZED IMPLANTABLE VASCULAR ACCESS PORT

CROSS-REFERENCE TO RELATED APPLICATIONS

This application is a divisional of U.S. patent application Ser. No. 11/651,770, filed on Jan. 9, 2007. This application claims benefit under Title 35, United States Code §119(e) of U.S. Provisional Application No. 60/757,417 filed on Jan. 10, 2006.

FIELD OF THE INVENTION

The following invention relates to implantable medical devices for subcutaneous implantation and which are placed into communication with a vascular structure, such as a vein, and which can be itself accessed through the skin, such as with a needle coupled to a syringe for delivery of therapeutic preparations into the vascular structure of the patient. More particularly, this invention relates to access ports which have an elongate form to minimize an incision size and which change in shape once implanted to exhibit a greater width and greater stability once implanted.

BACKGROUND OF THE INVENTION

Subcutaneously implanted vascular access devices, or ports, have been used for many years to provide long term vascular access in patients that require frequent or periodic therapeutic infusions or blood draws. Currently, ports generally have a body which contains a chamber accessible by a self-sealing septum and an outlet which is connected to a catheter which is placed into the vascular system. The base of the port is a generally flat side of the port which is intended to lie against the body, so the septum is generally oriented toward the skin surface. Many variations are possible. The septum may be convex or concave. The body may be plastic, metal or a combination of materials. The septum may be directly opposite the base, or may be angled relative to the base.

In current practice, the port is implanted into a subcutaneous pocket during a minor surgical procedure. One limitation to the development of smaller profile ports is the problem of port stability within the body after being placed. Ports in use currently may have a propensity to flip-over within the body if not sutured in place, rendering them inaccessible because the septum is facing down rather than up. The smaller the port, the greater the propensity to flip-over, and the harder it is to suture the port in place due to the smaller incision and smaller working pocket within which to suture. Thus, there is a need for a method to increase port stability while minimizing port implantation profile.

One such prior art port with a body that exhibits a generally elongate form and with an associated elongate septum is described in U.S. Pat. No. 6,213,973. While such a configuration does allow for a slightly minimized incision size, this prior art access port is not stabilized and is thus susceptible to "flipping-over" or otherwise rotating into an undesirable position.

Accordingly, a need exists for a vascular access port which provides both the benefit of stability once implanted and a small profile for insertion through a small incision, with the vascular access port being sufficiently small to allow for a minimization of size of the access port and other negative attributes associated with provision of such a vascular access port for the patient.

SUMMARY OF THE INVENTION

With this invention, a vascular access port is provided which uniquely includes a wing which can transition to a greater width than a width of a body of the access port. The wing, thus provides stability for the access port.

In a most preferred embodiment, the wing is an elongate structure pivotably mounted to a body of the access port, such as on an undersurface of the body. Upper surfaces of the body can be fitted with a chamber covered by a septum, with the septum held in place by a collar. The chamber can communicate with a vascular structure through a coupling in the port and an associated tube leading to the vascular structure. The body is typically elongate in form and the wing is also elongate in form. In a first position, the wing is aligned with the body so that the wing does appreciably enlarge a cross-sectional contour of the body, but can be passed through a small incision along with the elongate body.

Once implanted, the wing can rotate, preferably up to 90°, so that an elongate dimension of the wing is now provided lateral to the body with the body and wing together forming a somewhat "X" form. The wing and body thus provide a stable platform maintaining orientation of the septum facing the skin and ready for utilization. Most preferably, appropriate holes are provided in the body and wing through which sutures can pass. Such a suture line can be drawn tight once the port is implanted to cause the wing to rotate to its deployed position. The suture can then be tied off to keep the wing in its deployed position. When the access port is to be removed, the suture can be easily cut and removed. The wing can then be returned to its original position and the entire access port removed through a small removal incision in a manner the reverse of that associated with implantation of the access port. The access port could alternatively have two or more rigid wings which rotate in different directions to stabilize the access port.

In an alternative embodiment, the body can be formed within an elongate form and having a cavern therein near a lower surface of the body and with an end opening and at least two side openings. A deformable wing is provided which can be contracted laterally and expanded laterally in a resilient fashion. The wing has a width greater than the end opening of the cavern but can be contracted laterally sufficiently so that this deformable wing can fit through the end opening and into the cavern. Once the deformable wing is entirely inserted into the cavern, the deformable wing can expand to its original form, or beyond a width of its original form, so that a lateral width of the wing is expanded. With this embodiment the body would first be implanted. Next, the deformable wing would be implanted through the incision and into the end opening of the body, and into the cavern. Once the deformable wing is entirely inserted into the cavern, lateral portions of the wing expand to beneficially stabilize the access port for use.

OBJECTS OF THE INVENTION

Accordingly, a primary object of the present invention is to provide a vascular access port which can be implanted through a small incision.

Another object of the present invention is to provide a vascular access port which can be implanted subcutaneously and be easily used by a health care provider.

Another object of the present invention is to provide a vascular access port which can be implanted subcutaneously and which is of a small size, such that altered appearance of the patient is minimized by implantation of the access device.

Another object of the present invention is to provide a vascular access device which is stabilized after implantation to keep the vascular access device positioned where initially implanted and to discourage "rollover" or other undesirable repositioning of the vascular access port after implantation.

Another object of the present invention is to provide a method for stabilizing a vascular access port after it has been implanted subcutaneously.

Another object of the present invention is to provide a vascular access port which can be readily manufactured from available biocompatible materials and easily implanted and used by various health care personnel.

Other further objects of the present invention will become apparent from a careful reading of the included drawing figures, the claims and detailed description of the invention.

DESCRIPTION OF THE PREFERRED EMBODIMENT

Referring to the drawings, wherein like reference numerals represent like parts throughout the various drawing figures, reference numeral 10 is directed to a vascular access port which is adapted to be implanted subcutaneously and which can be stabilized once implanted by changing a shape of the port 10. In particular, the port 10 has a body 20 with a wing 70 that can be repositioned from a narrow initial orientation to a final wide orientation to enhance a lateral stability of the port 10. In this way, the port 10 is less susceptible to "rolling over" or other undesirable repositioning, while still being implantable through a small incision I in skin K for subcutaneous implantation in as minimally invasive a manner as possible.

Figure 14:
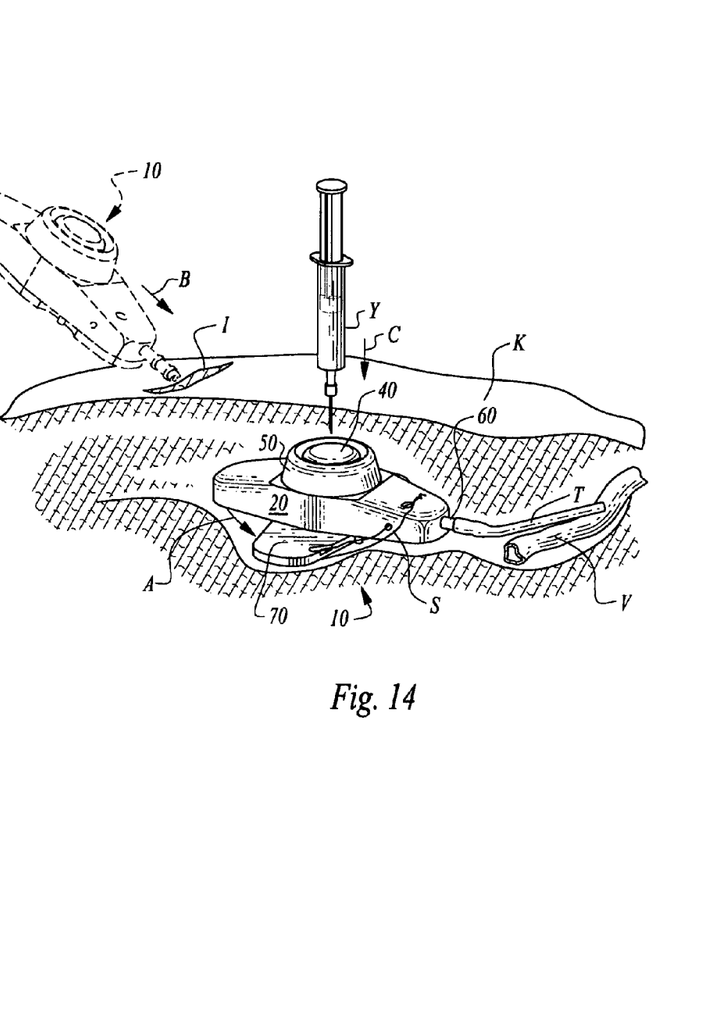
FIG. 14 is a perspective view of the port of this invention shown implanted within a body of a patient subcutaneously, and also showing in phantom the process by which the port is implanted into its final position, as well as how a syringe can access a vascular structure through the port.

In essence, and with particular reference to FIGS. 1-3 and 8, basic details of the port 10 of this invention are described, according to a preferred embodiment. The port 10 is primarily comprised of a body 20 which is elongate in a most preferred form. This body 20 includes a chamber 30 extending into the body 20. A septum 40 overlies this chamber 30. The septum 40 is of a character which allows a needle (such as that associated with a syringe Y) to penetrate the septum 40 (below the skin K) and gain access to the chamber 30, and which septum 40 reseals after needle removal. A collar 50 surrounds the septum 40 and secures the septum 40 over the chamber 30 and to the body 20. A coupling 60 acts as an interface out of a side of the port 10 to allow for fluid communication between the chamber 30 and a vascular structure, such as a vein V (FIG. 14).

An elongate wing 70 is also provided as part of the port 10, according to the preferred embodiment. This elongate wing 70 is pivotably coupled to the body 20, such as adjacent an undersurface 21 of the body 20. In the most preferred embodiment, a retainer 80 is provided to rotatably support the wing 70 on the body 20. The wing 70 can thus rotate from a first position aligned with the body 20 to a second position nonparallel with a long axis of the body 20, and preferably substantially perpendicular to the body 20. In this second deployed configuration, the port 10 is provided with enhanced lateral stability while still allowing the port 10 including both a body 20 and the wing 70 to fit through a relatively small incision I before deployment of the wing 70.

More specifically, and with particular reference to FIGS. 4-8 and 13, particular details of the body 20 are described. The body 20 is a substantially rigid unitary mass of material which is selected to be biocompatible and suitable for forming a major portion of the port 10. For instance, the body 20 could be formed of a biocompatible stainless steel, a biocompatible titanium alloy, or a sufficiently hard and rigid biocompatible plastic, composite, or other hard biocompatible material.

Figures 9, 10, 11, 12:
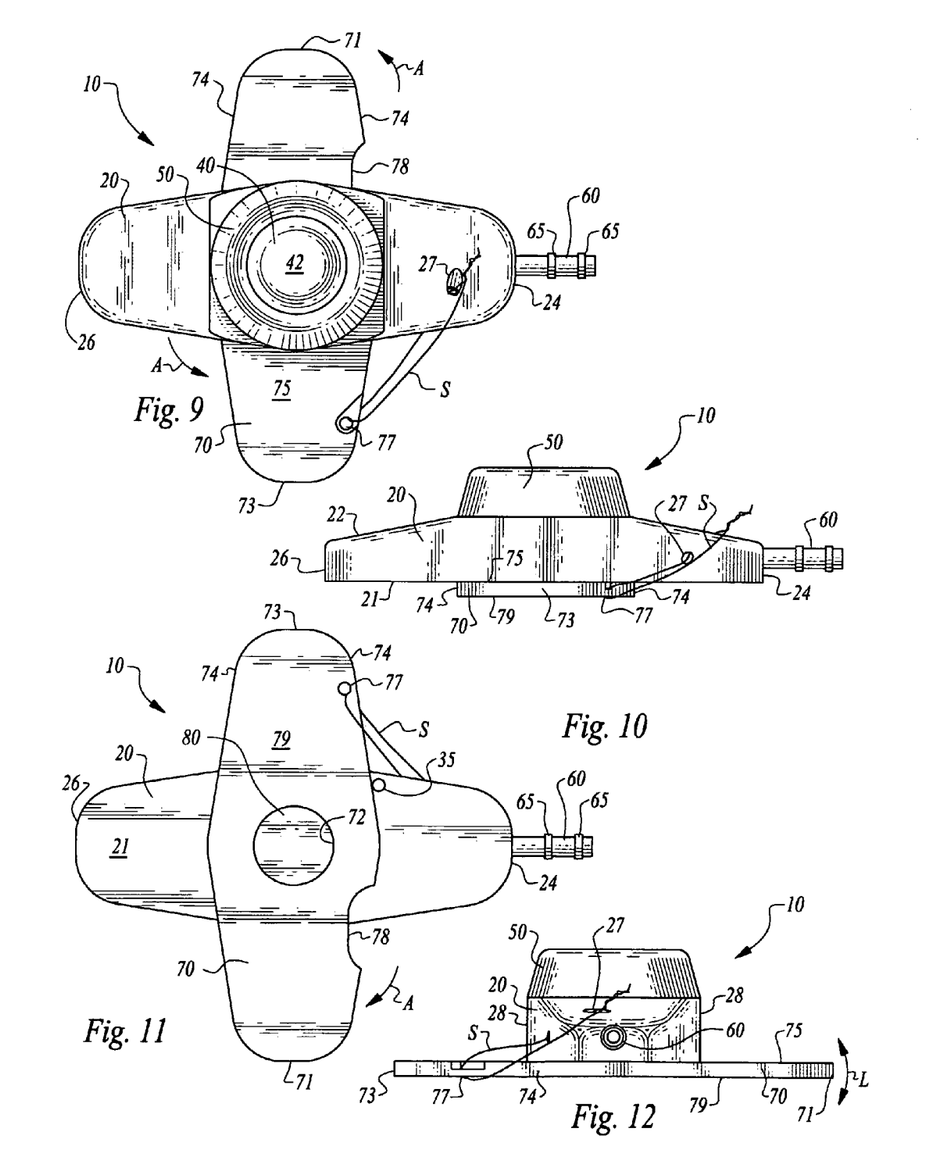
FIG. 9 is a top plan view of that which is shown in FIG. 3, with the wing fully deployed.
FIG. 10 is a side elevation view of that which is shown in FIG. 9.
FIG. 11 is a bottom plan view of that which is shown in FIG. 9.
FIG. 12 is an end elevation view of that which is shown in FIG. 9.

The body 20 could have a variety of different geometric outlines provided that it is configured to surround and form a perimeter for the chamber 30 and to hold the septum 40 and collar 50 upon the body 20. Most preferably, the body 20 is elongate in form with a length greater than a width. Such an elongate form allows the body 20 to fit through a relatively small incision I in the skin K (FIG. 14), while still having a relatively large size for stability. However, such stability provided by the body 20 alone only provides stability against rotation about one horizontal axis substantially perpendicular to a long axis of the elongate body 20 (resisting rotation along arrow L of FIG. 12). With the wing 70 deployed as described in detail below, full lateral stability can be provided in conjunction with the elongate body 20. As an alternative, the body 20 could be elongate or non-elongate and a pair of wings 70 could be provided, such as in the form of the dual wing port 110 (FIGS. 15 and 16) allowing for a high degree of stability with a smaller body 20.

With the elongate body 20, the length thereof between a first end 24 and second end 26 is preferably two to three times greater than the width between opposite sides 28. The body 20 has an upper surface 22 opposite an undersurface 21, with a height of the body 20 between the upper surface 22 and undersurface 21 generally similar to that of the width between the sides 28, but typically slightly less.

The body 20 has a recess 23 in the under surface 21 which receives a portion of the retainer 80 for support of the wing 70 in this preferred embodiment. A rim 25 surrounds this recess 23 to assist in aligning the wing 70 and retainer 80.

A tunnel 27 passes diagonally from the upper surface 22 to one of the sides 28 near the first end 24 of the body 20. This tunnel 27 allows suture S or other flexible line to pass therethrough as one portion of a method for drawing the wing 70 from a stored position to a deployed position, as described in detail below. The body 20 has a bore 29 extending from the chamber 30 to the first end 24. This bore 29 provides a preferred structure for fluid communication between the chamber 30 and out of the body 20 through the coupling 60. This bore 29 is preferably cylindrical and oriented parallel with the undersurface 21 of the body 20. The bore 29 can be stepped adjacent the first end 24 to allow the coupling 60 to fit into the bore 29 and minimize a transition in diameter between the bore 29 and a conduit 62 within the coupling 60.

The various surfaces of the body 20 are preferably tapered towards the ends 24, 26 to provide the body 20 with a somewhat streamlined appearance and to avoid the presentation of sharp or blunt edges which might make implantation of the port 10 through a small incision I more difficult or which might undesirably catch on internal bodily structures after implantation of the port 10.

Figures 1, 2:
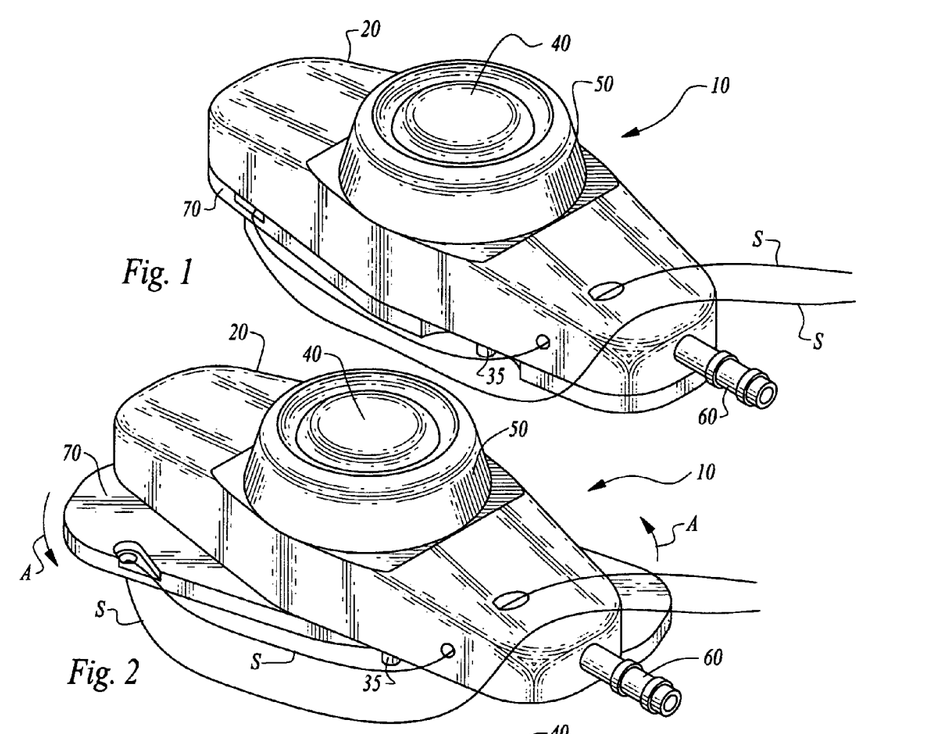
FIG. 1 is a perspective view of the stabilized implantable vascular access port of this invention before implantation and with a wing thereof aligned with a body thereof.
FIG. 2 is a perspective view of that which is shown in FIG. 1 and during rotation of a wing thereof from a first position aligned with the body and toward a second position skewed relative to the body.
Figure 3:
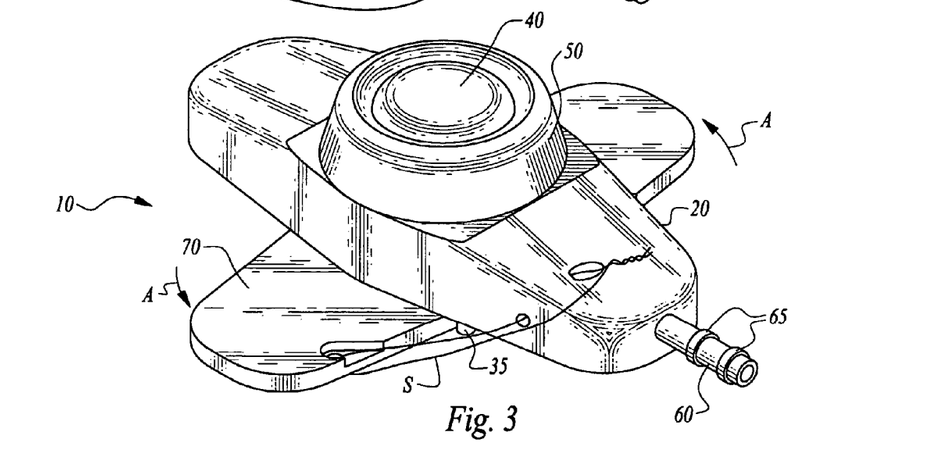
FIG. 3 is a perspective view of that which is shown in FIG. 1, but after the wing has been fully rotated to a final deployed position, with the wing substantially perpendicular to the elongate body, and with suture utilized to secure the wing in its deployed position.
Figure 4:
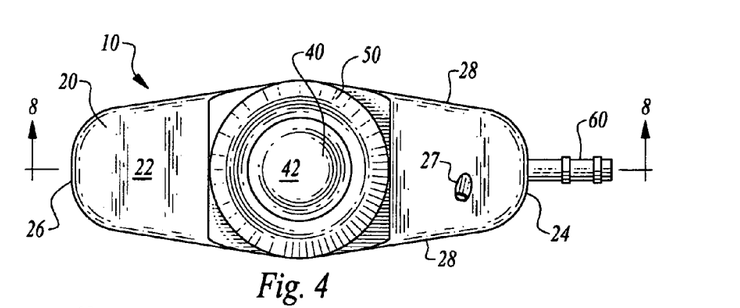
FIG. 4 is a top plan view of that which is shown in FIG. 1.
Figure 5:
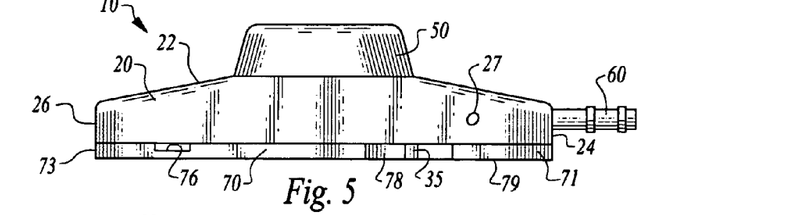
FIG. 5 is a side elevation view of that which is shown in FIG. 1.
Figures 6, 7:
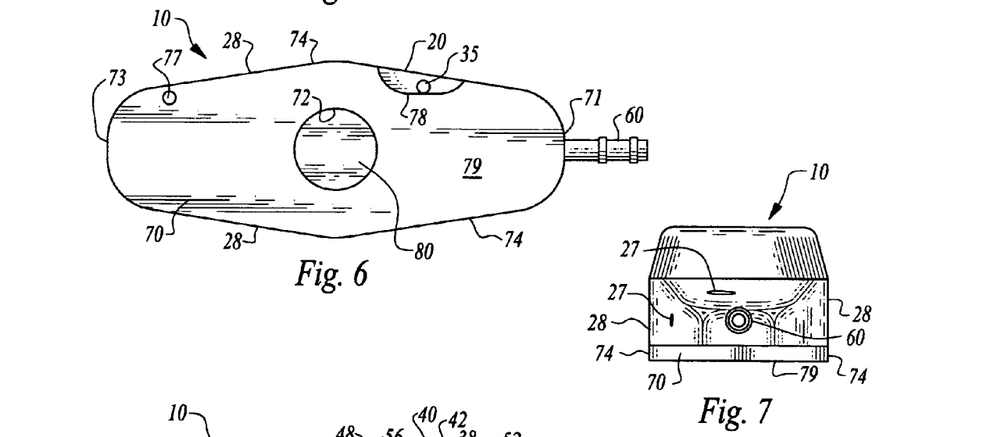
FIG. 6 is a bottom plan view of that which is shown in FIG. 1.
FIG. 7 is an end view of that which is shown in FIG. 1.
Figure 8:
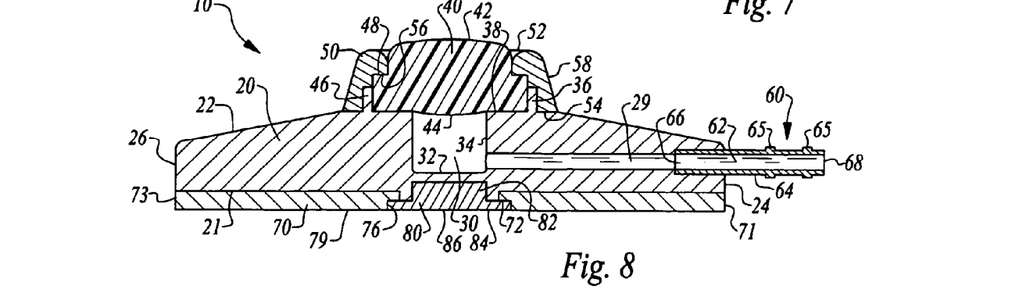
FIG. 8 is a full sectional view of that which is shown in FIG. 1.

With particular reference to FIG. 8, details of the chamber 30 within the body 20 are described. The chamber 30 defines a region into which medications or other fluid preparations are directed, when a needle passes through the septum 40 and into portions of the chamber 30 below the septum 40. These preparations can then pass from the chamber 30 out of the coupling 60 to the vascular structure (i.e. the vein V) with which the access port 10 has been associated for beneficial delivery to the patient. The chamber 30 is preferably a cylindrical blind bore that forms a recess extending substantially perpendicularly down through the upper surface 22 of the body 20 and stopping short of the undersurface 21 and stopping short of the recess 23 in the under surface 21. The chamber 30 is preferably aligned with the body 20 centrally and aligned with the recess 23 in the undersurface 21.

The chamber 30 preferably has a substantially flat floor 32 with cylindrical side walls 34 surrounding a floor 32. Walls of the chamber 30 are formed of a sufficiently hard material that the needle of the syringe Y (FIG. 14) does not penetrate out of the chamber 30, but rather a tip of the needle resides within the chamber 30 during delivery.

Other details of the body 20 include a ring 36 circumscribing the chamber 30 and extending vertically up from the upper surface 22. The ring 36 aligns the collar 50 around the septum 40 and facilitates a press fit or other fastening of the collar 50 to the body 20. An annular face 38 defines a portion of the upper surface 22 inside of the ring 36. This annular face 38 is generally annular in form and extends from the chamber 30 to the ring 36.

The undersurface 21 of the body 20 preferably includes a post 35 extending down perpendicularly from the undersurface 21. This post 35 is appropriately positioned so that when the wing 70 is rotated, a border 74 of the wing 70 abuts the post 35, when the wing 70 has been fully rotated to its deployed position. The post 35 thus acts as a stop for the wing 70 to prevent over-rotation of the wing 70.

Figure 13:
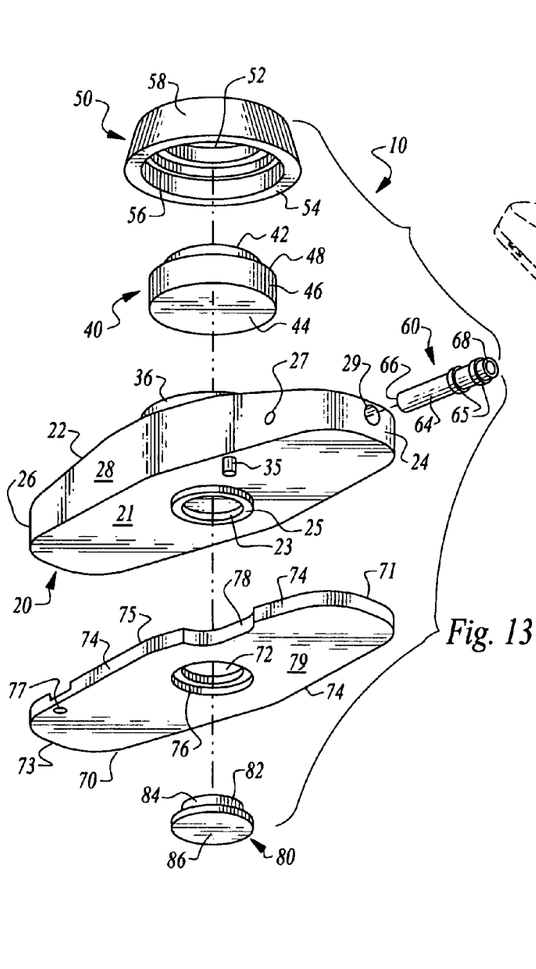
FIG. 13 is an exploded parts view of that which is shown in FIG. 1, showing how the various different parts of the vascular access device of this invention are joined together.

With particular reference to FIGS. 8 and 13, particular &tails of the septum 40 are described according to this preferred embodiment. The septum 40 is a monolithic semi-rigid mass of material which is typically formed of a silicone or other material which beneficially exhibits sufficient resiliency to allow a needle to pass therethrough repeatedly and to reseal numerous times before failure of the septum 40. The septum 40 preferably has a geometry similar to a space bounded by the chamber 30, ring 36 and collar 50 so that the septum 40 can seal off an upper end of the chamber 30 and be secured to the upper surface 22 of the body 20.

In particular, the septum 40 preferably includes a substantially planar top 42 opposite a substantially planar bottom 44. The top 42 can be slightly concave or convex if desired. The septum 40 is preferably generally cylindrical with a cylindrically curving perimeter 46 extending from the top 42 to the bottom 44. This perimeter 46 preferably includes a step 48 near the top 42 so that the top 42 has a lesser diameter than the bottom 44. The step 48 is complemental with structures on the collar 50 to further allow the septum 40 to be properly aligned with the collar 50 and secured to the body 20 by the collar 50.

The septum 40 is preferably slightly larger than the space provided for the septum 40 between the chamber 30, annular face 38, ring 36 and collar 50. In this way, the septum 40 is compressed slightly when in position adjacent the body 20. This causes the septum 40 to bulge upward somewhat at the top 42 and downward somewhat at the bottom 44 down into the chamber 30. The septum 40 can have an entirely planar bottom 44 resting upon the annular face 38 and overlying the chamber 30, or can be stepped to extend slightly into the chamber 30.

With particular reference to FIGS. 4-8 and 13, particular details of the collar 50 are described according to this preferred embodiment. The collar 50 is preferably a rigid band sized to be press fit over the septum 40 and the ring 36 to secure to the body 20 with a press fit and capture the septum 40 between the body 20 and the collar 50. The collar 50 includes an aperture 52 passing centrally therethrough. The aperture 52 is sized with a diameter similar to that of the top 42 of the septum 40. The collar 50 includes a foot 54 which is preferably substantially planar and annular, and adapted to abut the upper surface 22 of the body 20 just outside of the ring 36.

An inner contour 56 of the collar 50 extends from the foot 54 up to the aperture 52. This inner contour 56 has various transitions therein to accommodate the ring 36 of the body 20 and the step 48 of the septum 40 so that a substantially gapless fit is provided between the collar 50, the ring 36 and the septum 40. The inner contour 56 is preferably dimensioned to have an interference fit with the ring 36 of the body 20 to allow for the collar 50 to be press fit securely down onto the body 20 and over the ring 36. Similarly, the inner contour 56 of the collar 50 is preferably configured to have an interference fit with the top 42 and perimeter 46 of the septum 40, so that the collar 50 causes compression of the septum 40 somewhat.

The collar 50 has an outer surface 58 which is streamlined in form extending from the aperture 52 down to the foot 54. This streamlined contour further assists the body 20 in being easily inserted through a small incision I in the skin K (FIG. 14).

With particular reference to FIGS. 8 and 13, particular details of the coupling 60 are described according to this preferred embodiment. The coupling 60 is preferably a separate structure press fit to the body 20 or otherwise coupled to the body 20 and providing an interface through which tubing T can be coupled which extends between a vein V or other vascular structure and the coupling 60, so that a fluid pathway is provided between the port 10 and the vein V or other vascular structure of the patient. The tubing T can be sufficiently small to pass directly into the vascular structure or can be fitted with a needle or other vascular structure interface.

The coupling 60 is a generally cylindrical tubular rigid structure having a hollow interior defining a conduit 62. An outside surface 64 is also preferably cylindrical and sized to be press fit into the bore 29 where it exits the first end 24 of the body 20. This outside surface 64 preferably includes ribs 65 thereon which assist in retaining the tubing T upon the coupling 60. For instance, a retention band can be first placed over the tube T, the tube T can then be placed over the outside surface 64 of the coupling 60 and then the retention band can be drawn towards the body 20 until it resides over an outside surface of the tubing T and between the ribs 65 of the coupling 60, to securely hold the tubing T upon the conduit 60.

The coupling 60 includes an inside end 66 which is fixed within the body 20 and an outside end 68 opposite the inside end 66 and extending out of the body 20. The ribs 65 are located closer to the outside end 68 than to the inside end 66 with preferably about one-third of the coupling 60 retained within the body 20 and approximately two-thirds of the coupling 60 extending outside of the body 20.

With particular reference to FIGS. 8-13, particular details of the wing 70 are described according to this preferred embodiment. The wing 70 is preferably a rigid structure provided separate from the body 20, but pivotably attached to the body 20 through the retainer 80. The wing 70 most preferably has a plan form contour similar to that of the under surface 21 of the body 20, so that the wing 70 does not increase a width of the port 10 when the wing 70 is in a stored and collapsed initial orientation. The wing 70 extends from a first tip 71 to a second tip 73 with a length of the wing 70 between the tip 71, 73, similar to a length of the body 20 between the first end 24 and second end 26. The wing 70 includes an upper side 75 which is preferably adjacent to the undersurface 21 of the body 20 and a base surface 79 opposite the upper side 75 and defining a lowermost portion of the port 10.

An eyelet 77 preferably extends from the base surface 79 through the upper side 75. Where the eyelet 77 is provided, the upper side 75 is preferably cut away slightly to provide clearance for suture S passing through the eyelet 77 and for drawing the wing 70 from an initial stored orientation to a final deployed orientation. The wing 70 includes a central hole 72 through which the retainer 80 passes and through which the rim 25 of the body 20 passes, to keep the wing 70 aligned relative to the body 20 and allowing rotation of the wing 70. The border 74 defines a perimeter of the wing 70 which generally matches a perimeter of the body 20 in this preferred embodiment. A step 76 is preferably formed surrounding the hole 72 to allow the retainer 80 to hold the wing 70 adjacent the body 20.

A notch 78 is provided in a portion of the border 74 aligned with the post 35 extending down from the undersurface 21 of the body 20. This notch 78 allows the wing 70 to be completely rotated to its stored position without interference with the post 35.

In this preferred embodiment, the wing extends laterally in opposite directions to increase an overall width of the port 10 when the wing 70 has been deployed. Alternatively, some benefit would be provided by having a wing that is only about half of the length of the body 20 and which is only deployed laterally in one direction, or with two separate short wings with each of the wings deployed in opposite directions, with different embodiments providing a different degree of stability and complexity, as well as other unique attributes.

With particular reference to FIGS. 8 and 13, particular details of the retainer 80 are described according to this preferred embodiment. The retainer 80 is preferably a rigid mass coupled to the port 10 by press fitting into the recess 23 in the undersurface 21 of the body 20. The retainer 80 includes a central disk 82 which is cylindrical and sized to fit tightly within the recess 23. A flange 84 is below the central disk 82 and has a diameter greater than the central disk 82 and great enough to fit within the step 76 of the wing 70 and beyond a diameter of the hole 72 in the wing 70. A lower surface 86 of the retainer 80 is configured to be flush with the base surface 79 of the wing 70. With the retainer 80 in place, the wing 70 is free to rotate, but is restricted from translation along an axis of rotation of the wing 70 relative to the body 20.

Figure 15:
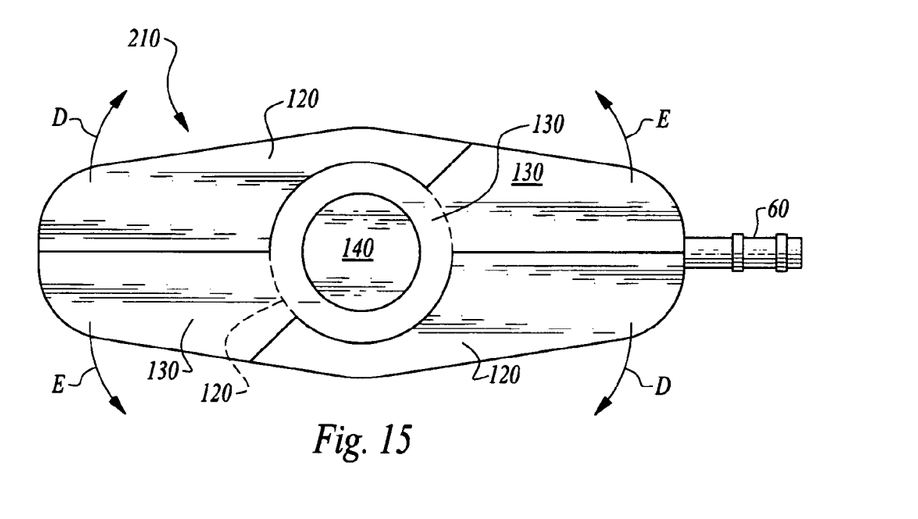
FIG. 15 is a bottom plan view of an alternative embodiment of that which is shown in FIG. 1, and having a pair of wings pivotably attached to the body of this embodiment.
Figure 16:
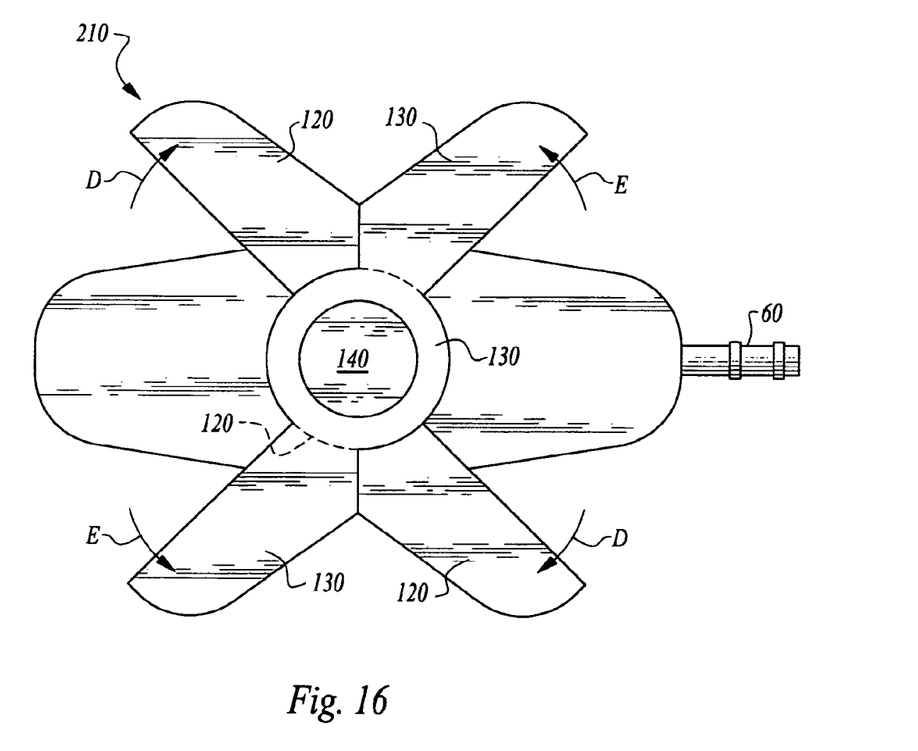
FIG. 16 is a bottom plan view similar to that which is shown in FIG. 15, but after rotation of the two wings of this port.

With particular reference to FIGS. 15 and 16, details of a dual wing port 110 are described defining an alternative embodiment of this invention. The dual wing port 110 has a body 20 (FIG. 16) which is preferably identical to the body 20 of the port 10, with the possible exception that the recess 23 and rim 25 could be slightly adjusted in size so that a pair of wings 120, 130 can be rotatably mounted to the body 20, rather than only a single wing 70, as described above and shown in FIGS. 1-14.

The dual wing port 110 includes a first wing 120 and a second wing 130 which are each pivotably attached to the body 20. Each of these wings 120, 130 is a separate rigid structure of elongate form and these wings 120, 130 are each held to the body 20 through a retainer 140 similar to the retainer 40 of the preferred embodiment. The retainer 140 might conceivably be slightly longer along a central axis thereof to accommodate the two wings 120, 130 sandwiched between the retainer 140 and the body 20.

The wings 120, 130 preferably are oriented at least partially within a common plane near tips of the wings 120, 130. Close the retainer 140, the second wing 130 is preferably closest to the lower face of the retainer 140 so that the second wing 130 goes underneath the first wing 120. The central portion of each of the wings 120, 130 is preferably annular in form with the first wing 120 configured to be above the second wing 130 and the second wing 130 configured to be below the first wing 120. The wings 120, 130 are then stepped as they extend radially out from the annulus with the first wing 120 stepping down slightly and the second wing 130 stepping up slightly and with both of the wings 120, 130 having a greater thickness away from the annular center portion than at the annular center portion. In this way, the wings 120, 130 have a common thickness and reside in a common plane on all parts thereof except for the annular center portion adjacent the retainer 140.

The wings 120, 130 are preferably configured to rotate in opposite directions. In particular, the first wing 120 is preferably configured to rotate clockwise (along arrow D of FIGS. 15 and 16). In contrast, the second wing 130 is preferably configured to rotate counter-clockwise (along arrow E of FIGS. 15 and 16). The wings 120, 130 are preferably configured so that after they rotate about 60°, they abut the other wing 120, 130 so that the wings 120, 130 each act as a stop to end rotation of the other wing 130, 120. With rotation completed, both the wings 120, 130 and the elongate body 20 act together to provide six peripheral points for a high degree of stability for the dual wing port 110.

With particular reference to FIGS. 17-20, particular details of a deformable wing port 210 of a further alternative embodiment, are described. The deformable wing port 210 does not have a rigid rotating wing, but rather has a deformable wing 250 which is capable of lateral contraction and expansion. The deformable wing port 210 features an alternative body 220. This alternative body is similar to the body 20 of the preferred embodiment on upper surfaces thereof and supports a similar chamber 30, septum 40, collar 50 and coupling 60, as described above with regard to the port 10 of the preferred embodiment. However, the wing 70 and retainer 80 of the preferred embodiment are not included with the deformable wing port 210. Instead, a cavern 230 is formed within the alternative body 220 close to but slightly spaced from a foot 240 defining a lowermost portion of the alternative body 220 and a lowermost portion of the deformable wing port 210. This foot 240 is spaced away from other portions of the alternative body 220 by the cavern 230.

The cavern 230 preferably has a substantially constant height between a ceiling 232 and a lower surface 234. The cavern 230 has side openings 235 which extend laterally outside of the alternative body 220 and an end opening 236 which extends out of an end of the alternative body 220 opposite the coupling 60. This end opening 236 could be reversed so that it is on a common end with the coupling 60 if desired.

The deformable wing 250 is preferably configured as a loop 252 which is formed within a plane similar in height to a height of the cavern 230, between the ceiling 232 and the lower surface 234. This loop 252 is preferably hollow in a middle thereof and so is formed with a plurality of legs 254 joined together at corners. The deformable wing 250 is preferably generally square in form so that it has four corners including a first corner 256, second corner 257, third corner 258 and fourth corner 259. A distance between the second corner 257 and fourth corner 259 defines a lateral width of the deformable wing 250. Material forming the deformable wing 250 is preferably deformable and resilient so that it maintains its original shape when unrestrained. For instance, the deformable wing 250 could be formed of a metal such as nickel titanium which can exhibit such characteristics.

Also, a thickness and/or width of the loop 252, and particularly adjacent the corners 256, 257, 258, 259 is selected to further facilitate such resilient deformability for the wing 250. In particular, the loop 252 forming the wing 250 can be narrower at the corners 256, 257, 258, 259 to facilitate bending. Such narrowing could be in thickness mostly (or entirely) with a height of the loop 252 substantially maintained. With such geometry, the loop 252 would relatively easily contract in width, but relatively greatly resist bending of the loop 252 out of the horizontal plane in which the loop 252 resides.

The deformable wing 250 is inserted into the alternative body 220 inside of the cavern 230 after the deformable wing port 210 has been implanted into the patient. The deformable wing 250 is merely provided to enhance stability of the deformable wing port 210. In particular, after the deformable wing port 210 has been positioned where desired, the end opening 236 of the cavern 230 extends generally toward the incision through which the deformable wing port 210 was implanted. The deformable wing 250 is then inserted through the incision and into the end opening 236 (along arrow F of FIG. 17). To allow the deformable wing 250 to pass through the incision with the incision having a small size, the deformable wing 250 is restrained, such as by being placed within a cannula or other restraint, so that the deformable wing 250 is contracted into a narrow lateral form (along arrow H of FIG. 18). The deformable wing 250 can then be fed through the incision and into the end opening 236 (along arrow G of FIG. 18) sufficient to allow the deformable wing 250 to pass entirely into the end opening 236 and into the cavern 230.

Once the deformable wing 250 has passed entirely into the cavern 230, the first corner 256 abuts a closed end 237 of the cavern 230. The lateral corners 257, 259 are then aligned with the side openings 235 and can resiliently extend laterally out of these side openings 235 to attain a wide lateral form (along arrow J of FIG. 19).

While the deformable wing 250 is preferably formed of an elastic and resilient material, it is conceivable that the deformable wing 250 could be deformed plastically to pass through the end opening 236 and then be caused to expand laterally (along arrow J) by having the first corner 256 abut the closed end 237 of the cavern and continuing to push on the third corner 258 until the second corner 257 and fourth corner 259 are bent and extend laterally out through the side openings 235 of the cavern 230. Hence, the deformable wing 250 could be both elastic and resilient or permanently bendable and still function somewhat according to this invention. If the deformable wing 250 is configured to be bendable, loads required to cause such bending are preferably sufficiently high so that the deformable wing 250 does not bend appreciably once implanted, such as when manipulated by a medical professional providing injections into the septum 40 of the deformable wing port 210.

Figure 17:
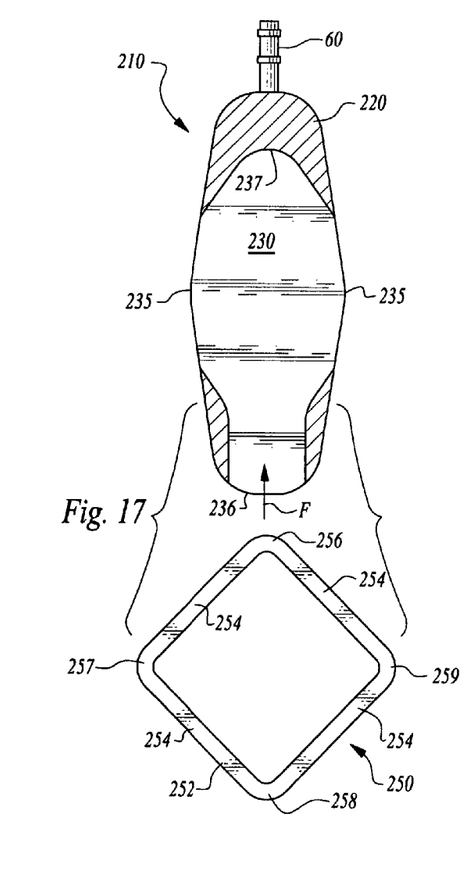
FIG. 17 is a sectional view of an alternative body and deformable wing of a deformable wing port embodiment of this invention with the deformable wing shown outside of a cavern within the deformable wing port and before insertion of the deformable wing.
Figure 18:
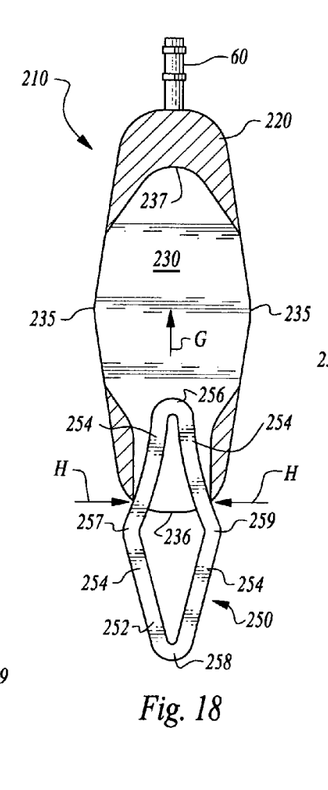
FIG. 18 is a sectional view similar to that which is shown in FIG. 17, but in the midst of the process of inserting the deformable wing into the cavern of the body of the deformable wing port.
Figure 19:
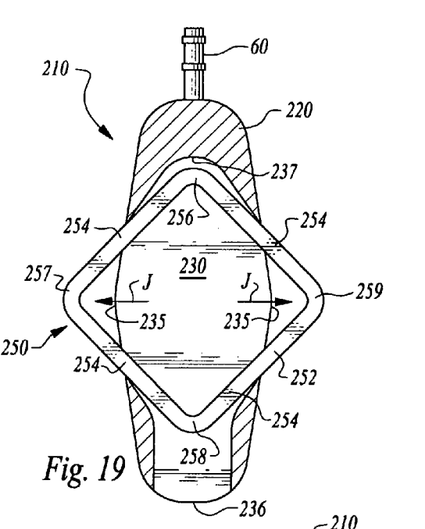
FIG. 19 is a full sectional view similar to that which is shown in FIG. 17, but after complete implantation of the deformable wing into the cavern of the deformable wing port.
Figure 20:
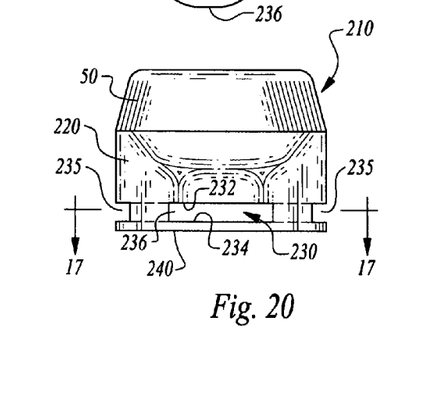
FIG. 20 is an end elevation view of the deformable wing port of FIGS. 17-19.

If desired, an end cap can be provided to close off the end opening 236, and to further push on the third corner 258 of the deformable wing 250. This end cap could also further stabilize the deformable wing 250, cause further lateral deployment of corners 257, 259 of the deformable wing 250 by pushing on the corner 258, and generally further enhance a stability of the deformable wing port 210. The deformable wing 250 depicted in FIGS. 17-19 exhibits a lateral width once expanded approximately twice a width of the alternative body 220 of the deformable wing port 210. If further lateral width expansion is desired for the deformable wing 250, the deformable wing 250 can be sized larger or can be provided with a diamond shape with a greater width between corners 257, 259 than length between corners 256, 258, so that when the deformable wing 250 has been fully inserted and is ready to be expanded laterally (along arrow J) the corners 257, 259 extend further from each other then as depicted in FIGS. 17-19. A size of the side openings 235 can also be correspondingly adjusted to accommodate the particular geometry of the deformable wing 250.

While the deformable wing 250 is shown as having four sides, the cavern 230 could have a variety of different numbers of openings and the deformable wing 250 could be a polygon having a variety of different numbers of corners and legs to provide a desired degree of stability.

In this deformable wing port 210 embodiment, the deformable wing 250 provides a convenient location where additional suturing can occur. For instance, if it is desirable that the deformable wing port 210 be sutured in place to further stabilize the deformable wing port 210, suturing can occur around legs 254 of the loop 252 where the deformable wing 250 extends out of the side openings 235, for secure suturing of the deformable wing port 210 into place. When removal of the deformable wing port 210 is desired, an appropriate tool can be provided which can pass into the end opening 236 and grip the third corner 258. By pulling on the third corner 258 while the body 220 is held stationary, the deformable wing 250 can then be removed out of the cavern 230 and pulled into a cannula or other restraint for effective removal out of a small incision. The body 220 can then also be removed through this same small incision.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. An implantable subcutaneous vascular access device, featuring a modifiable plan form, the access device comprising in combination:

a body having a recess therein;

said recess adapted to be brought into fluid communication with a vascular structure;

a septum covering an upper portion of said recess;

said septum adapted to allow a needle to penetrate said septum and to reseal after needle removal;

at least one wing adapted to have a variable lateral dimension that can be adjusted in lateral width to be greater than a width of said body, said wing movably coupled to said body with said wing extending laterally to stabilize the access device;

said body having an elongate form with a length greater than a width and greater than a height, said wing adapted to be positioned in a final position adjacent said body with a wing width greater than said width of said body, said wing having said height less than a height of said body before, during and after positioning of said wing adjacent to said body;

wherein said wing includes at least one deformable wing exhibiting a narrow lateral form and a wide lateral form, said deformable wing adapted to transition between said narrow lateral form and said wide lateral form, said wide lateral form wider than a width of said body; and wherein said body includes a cavern within an interior thereof, said cavern open to an exterior of said body through at least one end opening and two side openings generally opposite each other, said cavern having a height at least as great as a height of said at least one deformable wing, said cavern adapted to receive said deformable wing therein with portions of said deformable wing extending out of said side openings of said cavern.

2. An implantable subcutaneous vascular access device, featuring a modifiable plan form, the access device comprising in combination:

a body having a recess therein;

said recess adapted to be brought into fluid communication with a vascular structure;

a septum covering an upper portion of said recess;

said septum adapted to allow a needle to penetrate said septum and to reseal after needle removal;

at least one wing adapted to have a variable lateral dimension that can be adjusted in lateral width to be greater than a width of said body, said wing adapted to be attached to said body with said wing extending laterally to stabilize the access device;

wherein said wing includes at least one deformable wing exhibiting a narrow lateral form and a wide lateral form, said deformable wing adapted to transition between said narrow lateral form and said wide lateral form, said wide lateral form wider than a width of said body;

wherein said body includes a cavern within an interior thereof, said cavern open to an exterior of said body through at least one end opening and two side openings generally opposite each other, said cavern having a height at least as great as a height of said at least one deformable wing, said cavern adapted to receive said deformable wing therein with portions of said deformable wing extending out of said side openings of said cavern; and said deformable wing is formed as a loop with four separate sides joined together at corners, opposite corners of said loop being further from each other than a width of said loop when said deformable wing is in said wide lateral form, said opposite corners of said loop located closer to each other than a width of said end opening when said deformable wing is in said narrow form, with said deformable wing resiliently transitioning from said narrow form to said lateral form.

3. A method for stabilizing an implantable subcutaneous access port, the method including the steps of:

providing an access port having a body with a recess therein, the recess adapted to be brought into fluid communication with a vascular structure, a septum covering an upper portion of the recess, the septum adapted to allow a needle to penetrate the septum and to reseal after needle removal, and at least one wing having a lateral dimension greater than a width of the body, the wing adapted to be movably coupled to the body with the wing extending laterally to stabilize the access device, the body having an elongate form with a length greater than a width and greater than a height, the wing adapted to be positioned in a final position adjacent the body with a width greater than the width of the body, the wing having a height less than the height of the body before, during and after positioning of the wing adjacent to the body;

expanding the wing from a first width at least as narrow as the body to the final width wider than the body;

wherein said providing step includes the step of configuring the at least one wing to be a deformable wing and configuring the body to include a cavern therein having an end opening and two side openings passing into the cavern; and wherein said expanding step includes the step of contracting a width of the deformable wing, inserting the deformable wing into the cavern through the end opening and expanding the deformable wing at least partially out of side openings of the cavern in the body.

4. A method for stabilizing an implantable subcutaneous access port, the method including the steps of:

identifying an access port having a body with a recess therein, the recess adapted to be brought into fluid communication with a vascular structure, a septum covering an upper portion of the recess, the septum adapted to allow a needle to penetrate the septum and to reseal after needle removal, and at least one wing having a variable lateral dimension adjustable to be greater in lateral width than a width of the body, the wing adapted to be movably coupled to the body with the wing extending laterally to stabilize the access device, the wing exhibiting a narrow lateral form and a wide lateral form, the deformable wing adapted to transition between the narrow lateral form and the wide lateral form with the wide lateral form wider than a width of the body;

expanding the wing from a first narrow lateral form at least as narrow as the body to the final wide lateral form wider than the body;

wherein said identifying step includes the step of further identifying the at least one wing to be a deformable wing and the body to include a cavern therein having an end opening and two side openings passing into the cavern;

wherein said expanding step includes the step of contracting a width of the deformable wing, inserting the deformable wing into the cavern through the end opening and expanding the deformable wing at least partially out of side openings of the cavern in the body; and wherein said identifying steps include still further identifying the deformable wing being formed as a loop with four separate sides joined together at corners, opposite corners of the loop being further from each other than a width of the body when the deformable wing is in the wide lateral form, the opposite corners of the loop located closer to each other than a width of the end opening when the deformable wing is in the narrow form, with the deformable wing resiliently transitioning from the narrow form to the lateral form.

* * * * *